United States Patent [19]

Doll et al.

[11] Patent Number: 4,879,309

[45] Date of Patent: Nov. 7, 1989

[54] MERCAPTO-ACYLAMINO ACIDS AS ANTIHYPERTENSIVES

[75] Inventors: Ronald J. Doll, Maplewood; Bernard R. Neustadt, West Orange, both of N.J.

[73] Assignee: Schering Corporation, Kenilworth, N.J.

[21] Appl. No.: 304,881

[22] Filed: Jan. 30, 1989

Related U.S. Application Data

[63] Continuation-in-part of Ser. No. 250,035, Sep. 27, 1988, abandoned.

[51] Int. Cl.$^4$ .................. A61K 31/24; A61K 31/195; C07C 149/273
[52] U.S. Cl. ..................................... 514/513; 514/522; 514/535; 514/562; 514/616; 558/254; 558/416; 560/16; 560/17; 560/18; 562/427; 562/432; 564/153; 564/154
[58] Field of Search ................. 562/432, 427; 558/254, 558/416; 560/16, 17, 18; 564/153, 154; 514/513, 522, 535, 562, 616

[56] References Cited

U.S. PATENT DOCUMENTS

| | | | |
|---|---|---|---|
| 4,005,222 | 1/1977 | Martin et al. | 514/562 |
| 4,053,651 | 10/1977 | Ondetti et al. | 548/336 |
| 4,329,363 | 5/1982 | Dorn et al. | 514/562 |
| 4,329,495 | 5/1982 | Bindra . | |
| 4,401,677 | 8/1983 | Greenberg et al. | 424/317 |
| 4,513,009 | 4/1985 | Roques et al. | 514/513 |
| 4,740,499 | 4/1988 | Olins . | |
| 4,774,256 | 9/1988 | Delaney et al. | 514/513 |
| 4,801,609 | 1/1989 | Haslanger et al. | 562/547 |

FOREIGN PATENT DOCUMENTS

| | | |
|---|---|---|
| 38046 | 10/1981 | European Pat. Off. . |
| 136883 | 4/1985 | European Pat. Off. . |
| 0032260 | 2/1982 | Japan ................................. 514/562 |

OTHER PUBLICATIONS

Needleman et al., *N. Eng. J. Med.*, 314, 13(1986), pp. 828–834.
Cantin et al., *Sci. Amer.*, 254, (1986), pp. 76–81.
Wyuratt et al., *Med. Res. Rev.*, 5, (1985), pp. 483–531.

*Primary Examiner*—Mary C. Lee
*Assistant Examiner*—MarySue Howard
*Attorney, Agent, or Firm*—Anita W. Magatti; James R. Nelson; Stephen I. Miller

[57] ABSTRACT

Novel mercapto-acylamino acids useful as analgesic, as well as in the treatment of hypertension and congestive heart failure and combinations of mercapto acylamino acids and atrial natriuretic factors or angiotensin converting enzyme inhibitors useful for treating hypertension and congestive heart failure are disclosed.

16 Claims, No Drawings

MERCAPTO-ACYLAMINO ACIDS AS ANTIHYPERTENSIVES

This is a continuation-in-part of application Ser. No. 07/250,035 filed Sept. 27, 1988, now abandoned.

SUMMARY OF THE INVENTION

The present invention relates to mercapto-acylamino acids useful in the treatment of hypertension and congestive heart failure.

The invention also relates to the treatment of hypertension and congestive heart failure with a combination of a mercapto-acylamino acid and an atrial natriuretic factor (ANF) and with a combination of a mercapto-acylamino acid and an angiotensin converting enzyme (ACE) inhibitor.

Other aspects of the invention relate to pharmaceutical compositions comprising a mercapto-acylamino acid of this invention, alone or in combination with an ANF or an ACE inhibitor, and to methods of treatment of hypertension and congestive heart failure comprising administering a mercapto-acylamino acid of this invention, alone or in combination with an ANF or an ACE inhibitor to a mammal in need of such treatment.

BACKGROUND OF THE INVENTION

Still another aspect of the invention relates to a method of inhibiting the action of enkephalinase in a mammal thereby to elicit an analgesic effect with a mercapto-acylamino compound of this invention. Analgesic pharmaceutical compositions comprising said mercapto-acylamino compounds are also contemplated.

Human hypertension represents a disease of multiple etiologies. Included among these is a sodium and volume dependent low renin form of hypertension. Drugs that act to control one aspect of hypertension will not necessarily be effective in controlling another.

Enkephalin is a natural opiate receptor agonist which is known to produce a profound analgesia when injected into the brain ventricle of rats. If is also known in the art that enkephalin is acted upon by a group of enzymes known generically an enkephalinases, which are also naturally occurring, and is inactivated thereby.

A variety of mercapto-acylamino acids are known as enkephalinase inhibitors useful as analgesics and in the treatment of hypertension.

U.S. Pat. No. 4,513,009 to Roques et al. discloses, inter alia, compounds of the formula.

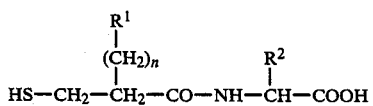

wherein n is 0 to 1; $R^1$ includes hydrogen, optionally substituted alkyl, optionally substituted phenyl, cyclohexyl and thienyl; and $R^2$ includes hydrogen optionally substituted alkyl, optionally substituted benzyl, phenyl, phenoxyalkyl and optionally substituted mercaptoalkyl. The compounds are disclosed as principally having enkephalinase activity, but also are said to be antihypertensives an analgesic.

U.S. Pat. No. 4,401,677 to Greenburg et al. and EPA 38,046 and Wilkinson disclose compounds of a scope similar to Roques et al, the former disclosing analgesic activity and the latter disclosing a greater specificity for enkephalinase than ACE. U.S. Pat. No. 4,053,651 to Ondetti et al. discloses the use of similar compounds in the treatment of renin-angiotensin related hypertension.

It has recently been discovered that the heart secretes a series of peptide hormones called atrial natriuretic factors (ANF) which help to regulate blood pressure, blood volume and the excretion of water, sodium and potassium. ANF were found to produce a short-term reduction in blood pressure and to be useful in the treatment of congestive heart failure. See P. Needleman et al., "Atriopeptin: A Cardiac Hormone Intimately Involved in Fluid, Electrolyte and Blood-Pressure Homeostasis", *N. Engl. J. Med.*, 314, 13 (1986) pp. 828–834, and M. Cantin et al in "The Heart as an Endocrine Gland", *Scientific American*, 254 (1986) pg, 76–81.

A class of drugs known to be effective in treating some types of hypertension is ACE inhibitors, which compounds are useful in blocking the rise in blood pressure caused by increases in vascular resistance and fluid volume due to the formation of angiotensin II from angiotensin I. For a review of ACE inhibitors, see M. Wyvratt and A. Patchett, "Recent Developments in the Design of Angiotensin Converting Enzyme Inhibitors" in *Med. Res. Rev.* Vol. 5, No. 4 (1985) pp. 483–531.

DETAILED DESCRIPTION

Nove antihypertensive compounds of the present invention are represented by the formula:

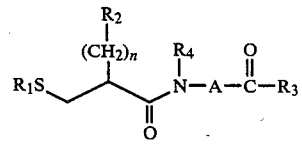

wherein
$R_1$ is H or $R_5CO—$;
$R_2$ is $Y—C_6H_4—$, $Y—C_6H_4S—$, $Y—C_6H_4O—$, $Y—C_6H_4CH_2S—$, $Y—C_6H_4CH_2O—$, α-naphthyl, β-naphthyl, furyl, thienyl, benzofuryl, benzothienyl, diphenylmethyl or

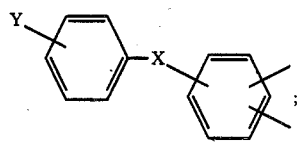

$R_3$ is $—OR_6$, $—NR_6R^7$ or

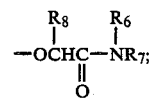

$R_4$ is hydrogen, lower alkyl or aryl lower alkyl;
$R_5$ is lower alkyl, hydroxylower alkyl, lower alkoxy lower alkyl; (di-lower alkyl) amino lower alkyl, $Y_1—C_6H_4$-lower alkyl, lower alkoxy, $Y_1—C_6H_4—$, naphthyl, furyl, thienyl or pyridyl;
$R_6$ and $R_7$ are independently hydrogen, lower alkyl or substituted lower alkyl wherein the substituents are selected from the group consisting of 1 or 2 hydroxy groups, 1 or 2 lower alkoxy groups, lower alkoxy lower alkoxy, halogeno, halogeno lower alkoxy, amino, mono- or di-lower; alkylamino, heterocycloalkyl, lower alkyl heterocycloalkyl, aryl, substituted aryl wherein the substituents on aryl are 1–3 substituents selected from the group consisting of lower alkyl, hydroxy, halogeno, lower alkoxy and amino, and a 5–6 membered saturated ring comprising 1–2 oxygen atoms as ring members wherein the ring carbon atoms are substituted with 0–2 lower alkyl substituents; or $R_6$ and $R_7$ together with the nitrogen to which they are attached complete a 5–7 membered ring, wherein 0–1 of the 4–6 ring members comprising $R_6$ and $R_7$ is a nitrogen atom, an alkyl-substituted nitrogen atom or an oxygen atom, and wherein the ring is substituted on the ring carbon atoms with 0–3 substituents selected from the group consisting of alkyl and hydroxy;

$R_8$ is hydrogen, alkyl, carboxyalkyl, mercaptoalkyl, alkylthioalkyl, aminoalkyl, hydroxyalkyl, phenylalkyl, hydroxyphenylalkyl, guanidinoalkyl, imidazolylalkyl, indolylalkyl or carbamoylalkyl;

n is 0–3;

A is

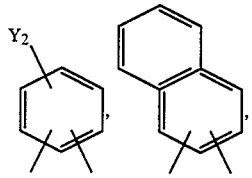

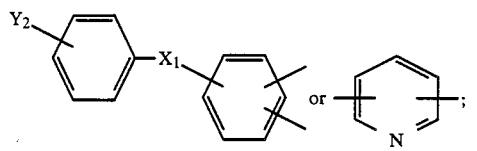

X and $X_1$ are independently a bond, —O—, —S—, or —CH$_2$—;

Y, $Y_1$ and $Y_2$ are independently 1 to 3 substituents selected from the group consisting of hydrogen, lower alkyl, cyclolower alkyl, lower alkoxy, OH, F, Cl, Br, I, —CN, —CO$_2$H, —CO$_2$-lower alkyl, —CH$_2$NH$_2$, —CONH$_2$ and aryl;

and the pharmaceutically acceptable acid addition salts thereof.

As used herein, the term "lower alkyl" means straight or branched alkyl chains of 1 to 6 1 carbon atoms, and "lower alkoxy" similarly refers to alkoxy groups having 1 to 6 carbon atoms. "Cyclolower alkyl" means cyclic alkyl groups of 3–6 carbon atoms.

"Heterocycloalkyl" means non-aromatic cyclic groups of 5–7 ring members wherein 1–3 of the ring members are independently selected from the group consisting of nitrogen, oxygen and sulfur. Examples of heterocycloalkyl groups are piperazinyl and morpholinyl groups.

"Aryl" means mono-cyclic or fused ring bicyclic carbocyclic aromatic groups having 6 to 10 ring members or mono-cyclic or fused ring bicyclic aromatic groups wherein 1–2 ring members are independently nitrogen, oxygen or sulfur. "Substituted aryl" are those groups wherein the carbon ring members may be substituted by one to three substituents selected from lower alkyl, hydroxy, halogeno, lower alkoxy and amino. Examples of carbocyclic aryl groups are phenyl, α-naphthyl and β-naphthyl, and examples of heterocyclic aryl groups are furyl, thienyl, benzofuryl, benzothienyl, indolyl and pyridyl. All positional isomers, e.g. 2-pyridyl, 3-pyridyl, are contemplated.

"Halo" refers to fluorine, chlorine, bromine or iodine radicals.

Preferred compounds of the present invention are those wherein $R_2$ is Y—C$_6$H$_4$—. Also preferred are those compounds of formula I wherein $R_4$ is hydrogen. A third preferred group is that wherein n is 1. Another group of preferred compounds is that wherein $R_3$ is —OR$_6$, especially wherein $R_6$ is hydrogen; —NR$_6$R$_7$, especially wherein $R_6$ and $R_7$ are each hydrogen or one of $R_6$ and $R_7$ is hydrogen and the other is aryl lower alkyl, heterocycloalkyl or heterocycloalkyl lower alkyl; or $R_6$ and $R_7$ and the nitrogen to which they are attached form a ring. Examples of preferred —NR$_6$R$_7$ groups are amino, 2-(4-morpholinyl)ethylamino, 2-(4-pyridinyl)ethylamino and 4-methyl-1-piperazinyl. Still another group of preferred compounds is that wherein A is phenyl, i.e.

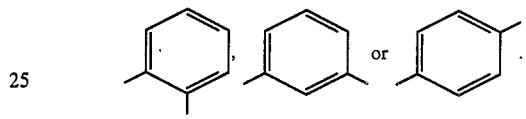

Preferred substituents at $R_1$ are hydrogen, acetyl and benzoyl.

Compounds of this invention may, depending on the nature of functional groups, form addition salts with various inorganic and organic acids and bases. Such salts include salts prepared with organic and inorganic acids, e.g. HCl, HBr, H$_2$SO$_4$, H$_3$PO$_4$, methanesulfonic acid, toluenesulfonic acid, maleic acid, fumaric acid and camphorsulfonic acid. Salts prepared with bases include ammonium salts, alkali metal salts, e.g. sodium and potassium salts, and alkaline earth salts, e.g. calcium and magnesium salts.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Compouds of formula I have at least one asymmetrical carbon atom and therefore include various stereoisomers. All stereoisomers are included within the scope of the present invention.

Compounds of the present invention can be made by methods well known to those skilled in the art. A typical general procedure is to convert a substituted propionic acid to the corresponding acid chloride and to react said acid chloride with an aminoaryl acid or aminoaryl amide in the presence of a base such as pyridine, as shown in the following reaction scheme:

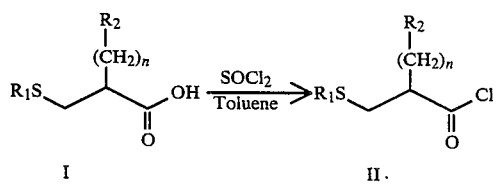

-continued

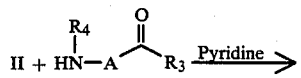

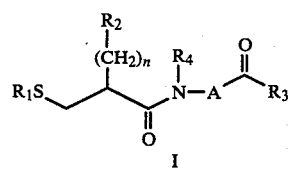

In the reaction scheme above, $R_1$ is typically acetyl or benzoyl. To obtain compounds of formula I wherein $R_1$ is hydrogen, the sulfur protecting group can be removed by conventional means, e.g. removal of an acetyl or benzoyl group can be accomplished by treating with sodium hydroxide, then acidifying with HCl.

Alternatively, intermediates of formulae I and III can be coupled directly using reagents well known in the peptide art, e.g. dicyclohexylcarbodimide.

A second aspect of the invention is the administration of a combination of an ANF and a compound of formula I for the treatment of hypertension.

As indicated by Needleman et al., a number of ANF have been isolated so far, all having the same core sequence of 17 amino acids within a cysteine disulfide bridge, but having different N-termini lengths. These peptides represent N-terminal truncated fragments (21–48 amino acids) of a common preprohormone (151 and 152 amino acids for man and rats, respectively). Human, porcine and bovine carboxy-terminal28-amino acid peptides are identical and differ from similar peptides in rats and mice in that the former contain a methionine group at position 12 while the latter contain isoleucine. Various synthetic analogs of naturally occuring ANF's also have been found to have comparable biological activity. Examples of ANFs contemplated for use in this invention are α human AP 21 (atriopeptin I), α human AP 28, α human AP 23 (atriopeptin II or APII), α human AP 24, α human AP 25, α human AP26, α human AP 33, and the corresponding rat sequence of each of the above wherein Met 12 is Ile. See Table 1 for a comparison of the peptides.

TABLE 1

| | HUMAN PEPTIDE | | | | | |
|---|---|---|---|---|---|---|
| AP 33 | AP 28 | AP 26 | AP 25 | AP 24 | AP 23 | AP 21 |
| Leu | | | | | | |
| Ala | | | | | | |
| Gly | | | | | | |
| Pro | | | | | | |
| Arg | | | | | | |
| Ser | Ser | | | | | |
| Leu | | | | | | |
| Arg | | Arg | | | | |
| Arg | | | Arg | | | |
| Ser | | | | Ser | Ser | Ser |
| Ser | | | | | | |
| Cys—S | | | | | | |
| Phe | | | | | | |
| Gly | | | | | | |
| Gly | | | | | | |
| Arg | | | | | | |
| Met* | | | | | | |
| Asp | | | | | | |
| Arg | | | | | | |
| Ile | | | | | | |
| Gly | | | | | | |
| Ala | | | | | | |
| Gln | | | | | | |
| Ser | | | | | | |
| Gly | | | | | | |
| Leu | | | | | | |
| Gly | | | | | | |
| Cys—S | | | | | | |
| Asn | | | | | | |
| Ser | | | | | | Ser |
| Phe | | | | | | |
| Arg | | | | | Arg | |
| Tyr | Tyr | Tyr | Tyr | Tyr | | |

*Ile in the rat peptide

A third aspect of the invention in the administration of a combination of an ACE inhibitor and a compound of formula I.

Examples of ACE inhibitors are those disclosed in the article by Wyvratt et al., cited above, and in the following U.S. patents: U.S. Pat. Nos. 4,105,776, 4,468,519, 4,555,506, 4,374,829, 4,462,943, 4,470,973, 4,470,972, 4,350,704, 4,256,761, 4,344,949, 4,508,729, 4,512,924, 4,410,520 and 4,374,847, all incorporated herein by reference; and the following foreign patents or published patent applications:

British Specification No. 2095682 published Oct. 6, 1982 discloses N-substituted-N-carboxyalkyl aminocarbonyl alkyl glycine derivatives which are said to be angiotensin converting enzyme inhibitors and have the formula

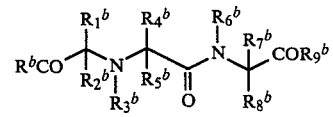

either (A) $R^b$ and $R_9^b$ are OH, 1–6C alkoxy, 2–6C alkenyloxy, di-(1–6C alkyl)amino-(1–6C) alkoxy, 1–6C hydroxyalkoxy, acylamino-(1–6C)alkoxy, acyloxy-(1–6C)alkoxy, aryloxy, aryloxy-(1–6C)alkoxy, $NH_2$, mono- or di-(1–6C alkyl)amino, hydroxyamino or aryl-(1–6C)alkylamino;

$R_1^b$–$R_5^b$, $R_7^b$ and $R_8^b$ are 1–20C alkyl, 2–20C alkenyl, 2–20C alkynyl, aryl, aryl-(1–6C) alkyl having 7–12C or heterocyclyl-(1–6C)alkyl having 7–12C;

$R_6^b$ is cycloalkyl, polycycloalkyl, partly saturated cycloalkyl or polycycloalkyl, cycloalkyl-(1–6C)alkyl having 3–20C, 6–10C aryl, aryl-(1–6C)alkyl, aryl-(2–6C)alkenyl or aryl-(2–6C) alkynyl;

or $R_2^b$ and $R_3^b$ together with the C and N atoms to which they are attached or $R_3^b$ and $R_5^b$ together with the N and C atoms to which they are attached form an N-heterocycled containing 3–5C or 2–4C and a S atom;

all alkyl, alkenyl and alkynyl are optionally substituted by OH, 1–6C alkoxy, thio(sic), 1–6C alkylthio, $NH_2$, mono- or di(1–6C alkyl)amino, halogen or $NO_2$;

all 'cycloalkyl' groups (including poly and partially unsaturated) are optionally substituted by halogen, 1-6C hydroxyalkyl, 1-6C alkoxy, amino-(1-6C alkyl)amino, di-(1-6C alkyl)amino, SH, 1-6C alkylthio, $NO_2$ or $CF_3$;

and aryl groups are optionally substituted by OH, 1-6C alkoxy, $NH_2$, mono- or di-(1-6C alkyl) amino, SH, 1-6C alkylthio, 1-6C hydroxyalkyl, 1-6C aminoalkyl, 1-6C thioalkyl, $NO_2$, halogen, $CF_3$, $OCH_2O$, ureido or guanidino;

or (B) $R^b$ and $R_9^b$ are H or 1-6C alkoxy;

$R_1^b$ and $R_2^b$ are H, 1-6C alkyl, aryl-(1-6C) alkyl having 7-12C or heterocyclyl-(1-6C) alkyl having 6-12C;

$R_3^b$-$R_5^b$, $R_7^b$ and $R_8^b$ are H or 1-6C alkyl;

$R_6^b$ is cycloalkyl, polycycloalkyl, partly saturated cycloalkyl or polycycloalkyl, cycloalkyl-(1-6C) alkyl having 3-20C, aryl or aryl-(1-6C) alkyl;

and aryl has 6-10C and is optionally substituted by 1-6C alkyl, 2-6C alkenyl, 2-6C alkynyl, OH, 1-6C alkoxy, $NH_2$, mono- or di-(1-6C alkyl) amino, SH, 1-6C alkylthio, 1-6C hydroxyalkyl, 1-6C aminoalkyl, 1-6C thioalkyl, $NO_2$, halogen, $CF_3$, $OCH_2O$, ureido or guanidino;

European Patent Application No. 0 050 800 published May 5, 1982 discloses carboxyalkyl dipeptides derivatives which are said to be angiotensin converting enzyme inhibitors and have the formula

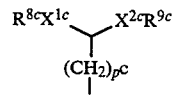

or a pharmaceutically acceptable salt thereof, wherein $R^c$ and $R^{6c}$ are the same or different and are hydroxy, lower alkoxy, lower alkenyloxy, dilower alkylamino lower alkoxy, acylamino lower alkoxy, acyloxy lower alkoxy, aryloxy, aryllower alkoxy, amino, lower alkylamino, dilower alkylamino, hydroxyamino, aryllower alkylamino, or substituted aryloxy or substituted aryllower alkoxy wherein the substituentis methyl, halo or methoxy; $R^{1c}$ is hydrogen, alkyl of from 1 to 10 carbon atoms, substituted lower alkyl wherein the substituent is hydroxy, lower alkoxy, aryloxy, substituted aryloxy, heteroaryloxy, substituted heteroaryloxy, amino, lower alkylamino, diloweralkylamino, acylamino, arylamino, substituted arylamino, guanidino, imidazolyl, indolyl, lower alkylthio, arylthio, substituted arylthio, carboxy, carbamoyl, lower alkoxy carbonyl, aryl, substituted aryl, aralkyloxy, substituted aralkyloxy, aralylthio or substituted aralkylthio, wherein the aryl or heteroaryl portion of said substituted aryloxy, heteroaryloxy, arylamino, arylthio, aryl, aralkyloxy, aralkylthio group is substituted with a group selected from halo, lower alkyl, hydroxy, lower alkoxy, amino, aminomethyl, carboxyl, cyano, or sulfamoyl; $R^{2c}$ and $R^{7c}$ are the same or different and are hydrogen or lower alkyl; $R^{3c}$ is hydrogen, lower alkyl, phenyl lower alkyl, aminoethyl- phenyl lower alkyl, hydroxyphenyl lower alkyl, hydroxy lower alkyl, acylamino lower alkyl, amino lower alkyl, dimethylamino lower alkyl, guanidino lower alkyl, imidazolyl lower alkyl, indolyl lower alkyl, or lower alkyl thio lower alkyl; $R^{4c}$ and $R^{5c}$ are the same or different and are hydrogen, lower alkyl or $Z^c$, or $R^{4c}$ and $R^{5c}$ taken together form a group represented by $Q^c$, $U_c$, $V_c$, $Y^c$, $D^3$or $E^c$, wherein; $Z^c$ is

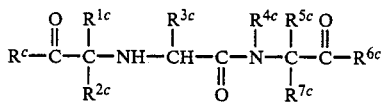

wherein $X^{1c}$ and $X^{2c}$ independent of each other are O, S or $CH_2$, $R^{8c}$ and $R^{9c}$ independent of each other are lower alkyl, lower alkenyl, lower alkynyl, cycloalkyl having 3 to 8 carbon atoms, hydroxy lower alkyl, or $-(CH_2)_{n^c}Ar^c$, wherein $n^c$ is 0, 1, 2 or 3 and $Ar^c$ is unsubstituted or subsituted phenyl, furyl, thienyl or pyridyl, wherein said substituted phenyl, furyl, thienyl or pyridyl groups are substituted with at least one group that is independently selected from $C_1$ to $C_4$ alkyl, lower alkoxy, lower alkylthio, halo, $CF_3$ and hydroxy, or $R^{8c}$ and $R^{9c}$ taken together form a bridge $W^c$, wherein $W^c$ is a single bond or a methylene bridge or a substituted methylene bridge when at least one of $X^{1c}$ and $X^{2c}$ is methylene, or $W^c$ is an alkylene or substituted alkylene bridge having 2 or 3 carbon atms, said substituted methylene bridge or said substituted alkylene bridge having one or two substituents selected from lower alkyl, aryl and aryl lower alkyl groups, and $p^c$ is 0, 1 or 2; with the proviso that at least one of $R^{4c}$ and $R^{5c}$ is $Z^c$, with the proviso that if $R^{4c}$ is $Z^c$ and $p^c$ is 0 then $X^{1c}$ and $X^{2c}$ must both be methylene, and with the proviso that if $X^{1c}$ and $X^{2c}$ are both methylene then $R^{8c}$ and $R^{9c}$ must form an alkylene bridge $W^c$; $Q^c$ is

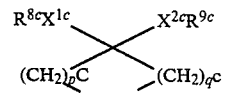

wherein $R^{8c}$, $R^{9c}$, $X^{1c}$ and $X^{2c}$ are as defined above, $p^c$ is 0, 1 or 2, $q^c$ is 0, 1 or 2, with the proviso that the sum of $p^c$ and $q^c$ must be 1, 2 or 3, with the proviso that if $p^c$ is 0 then $X^{1c}$ and $X^{2c}$ mut be methylene, and with the proviso that if $X^{1c}$ and $X^{2c}$ are methylene then $R^{8c}$ and $R^{9c}$ taken together form a bridge $W^c$, wherein $W^c$ is as defined above; $V^c$ is

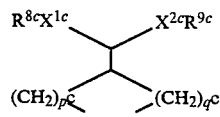

wherein $R^{8c}$, $R^{9c}$, $X^{1c}$ and $X^{2c}$ are as defined above, $p^c$ is 0, 1 or 2 and $q^c$ is 0, 1 or 2, with the proviso that the sum of $p^c$ and $q^c$ is 1, 2 or 3, with the proviso that if $X^{1c}$ and $X^{2c}$ are $CH_2$ then $R^{8c}$ and $R^{9c}$ taken together form a bridge $W^c$, wherein $W^c$ is as defined above; $U^c$ is

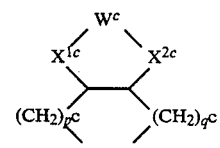

wherein $W^c$ is as defined above (except that $W^c$ may also be a methylene bridge when $X^{1c}$ and $X^{2c}$ are oxygen or sulfur), $X^{1c}$ and $X^{2c}$ are as defined above, $p^c$ is 0, 1 or 2, $q^c$ is 0, 1 or 2, with the proviso that the sum of $p^c$ and $q^c$ is 1 or 2, and with the proviso that if $p^c$ is 0, $X^{1c}$ must be $CH_2$; $Y^c$ is is

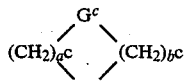

wherein $G^c$ is oxygen, sulfur or $CH_2$, $a^c$ is 2, 3 or 4 and $b^c$ is 1, 2, 3, 4 or 5, with the proviso that the sum of $a^c$ and $b^c$ is 5, 6 or 7 or $G^c$ is $CH_2$, $a^c$ is 0, 1, 2 or 3, $b^c$ is 0, 1, 2 or 3 with the proviso that the sum of $a^c$ and $b^c$ is 1, 2 or 3, with the proviso that the sum of $a^c$ and $b^c$ may be 1, 2 or 3 only if $R^{1c}$ is lower alkyl substituted with aralkylthio or aralkyloxy; $D^c$ is

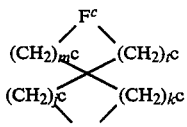

wherein $F^c$ is O or S, $j^c$ is 0, 1 or 2 and $k^c$ is 0, 1 or 2, with the proviso that the sum of $j^c$ and $k^c$ must be 1, 2 or 3, and $m^c$ is 1, 2 or 3 and $t^c$ is 1, 2 or 3, with the proviso that the sum of $m^c$ and $t^c$ must be 2, 3 or 4; $E^c$ is

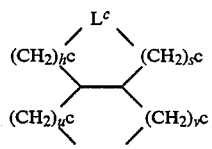

wherein $L^c$ is O or S, $u^c$ is 0, 1 or 2 and $v^c$ is 0, 1 or 2, with the proviso that the sum of $u^c$ and $v^c$ must be 1 or 2, and $h^c$ is 1 or 2 and $s^c$ is 1 or 2, with the proviso that the sum of $h^c$ and $s^c$ must be 2 or 3;

European patent application 0 079 522 published May 25, 1983 discloses N-carboxymethyl(amidino) lysylproline compounds which are said to be angiotensin converting enzyme inhibitors and have the formula where

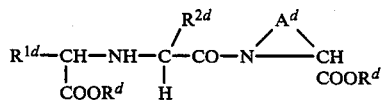

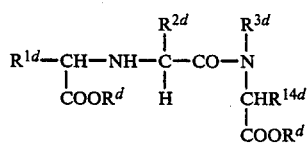

wherein:

$R^d$ and $R^{2d}$ are independently hydrogen; loweralkyl; aralkyl; or aryl; $R^{1d}$ is hydrogen; branched or straight chain $C_{1-12}$ alkyl and alkenyl; $C_3$-$C_9$ cycloalkyl and benzofused alkyl; substituted loweralkyl where the substituents are halo, hydroxy loweralkoxy, aryloxy, amino, mono- or diloweralkylamino, acylamino, arylamino, guanidino, mercapto, loweralkylthio, arylthio, carboxy, carboxamido, or lowerallkoxycarbonyl; aryl; substituted aryl where the substituents are loweralkyl, loweralkoxy, or halo; arloweralkyl; arloweralkenyl; heteroarloweralkyl; heteroarloweralkenyl; substituted arloweralkyl, substituted arloweralkenyl, substituted heteroarloweralkyl, or substituted heteroarloweralkenyl where the aryl and heteroaryl substituents are halo, dihalo, loweralkyl, hydroxy, loweralkoxy, amino, aminoloweralkyl, acylamino, mono- or diloweralkylamino, carboxyl, haloloweralkyl, nitro, cyano, or sulfonamido, and where the loweralkyl portion of arloweralkyl may be substituted by amino, acylamino, or hydroxyl;

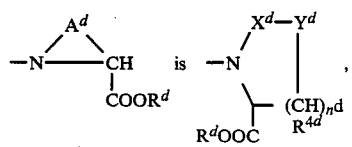

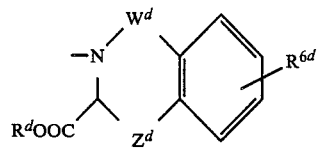

or

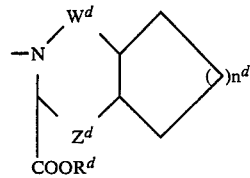

where:

$X^d$ and $Y^d$ taken together are —$CH_2$—$CH_2$—;

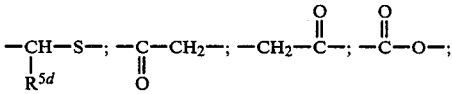

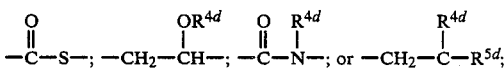

$R^{4d}$ is hydrogen; loweralkyl; aryl; substituted aryl;
$R^{5d}$ is hydrogen; loweralkyl; aryl or substituted aryl;
$n^d$ is 1 to 3;
$W^d$ is absent; —$CH_2$—; or

$Z^d$ is —$(CH_2)_{m^d}$, where $m^d$ is 0 to 2, provided that $m^d$ may not be 0 and $W^d$ may not be absent at the same time; and $R^{6d}$ is hydrogen; loweralkyl; halo; or $OR^{4d}$;
$R^{2d}$ is —$(CH_2)_{r^d}$—$B^d$—$(CH_2)_{s^d}$—$NR^{7d}R^{15d}$
where
$r^d$ and $s^d$ are independently 0 to 3;
$B^d$ is absent; —O—; —S—; or —$NR^{8d}$;
where $R^{8d}$ is hydrogen; loweralkyl; alkanoyl; or aroyl; and
$R^{7d}$ is

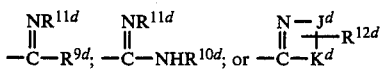

where

R$^{9d}$ is loweralkyl; aralkyl; aryl; heteroaryl; or heteroarloweralkyl and these groups substituted by hydroxy, lower alkoxy or halo; carboxyl; carboxamido; nitromethenyl.

R$^{10d}$ is hydrogen; loweralkyl; aryl; or amidino;

R$^{11d}$ hydrogen; loweralkyl; cyano; amidino; aryl; aroyl; loweralkanoyl;

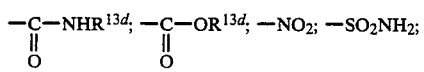

or SO$_2$R$^{13d}$;

R$^{12d}$ is hydrogen; loweralkyl; halo; aralkyl; amino; cyano; mono- or diloweralkylamino; or OR$^{4d}$;

R$^{13d}$ is hydrogen; loweralkyl; or aryl;

R$^{15d}$ is hydrogen; lower alkyl; aralkyl; or aryl;

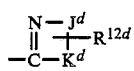

constitute a basic heterocycle of 5 or 6 atoms or benzofused analogs thereof and optionally containing 1-3N atoms, an oxygen, a sulfur, an S=O, or an SO$_2$ group optionally substituted by amino, lower alkyl amino, diloweralkyl amino, lower alkoxy, or aralkyl groups;

R$^{3d}$ is C$_{3-8}$ cycloalkyl and benzofused C$_{3-8}$ cycloalkyl; perhydrobenzofused C$_{3-8}$ cycloalkyl; aryl; substituted aryl; heteraryl; substituted heteroaryl;

R$^{14d}$ is hydrogen or loweralkyl; and, a pharmaceutically acceptable salt thereof;

European Patent 79022 published May 18, 1983 discloses N-amino acyl-azabicyclooctane carboxylic acid derivatives which have the formula

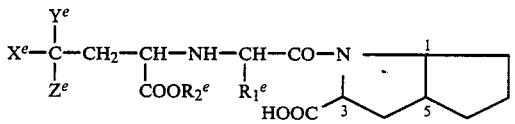

hydrogen atoms at ring positions 1 and 5 are cis to each other and the 3-carboxy group has the endo orientation;

R$_1^e$ is H, allyl, vinyl or the side chain of an optionally protected naturally occurring α-amino acid;

R$_2^e$ is H, 1-6C alkyl, 2-6C alkenyl or aryl(1-4C alkyl);

Y$^e$ is H or OH and Z$^e$ is H, or Y$^e$ and Z$^e$ together oxygen;

X$^e$ is 1-6C alkyl, 2-6C alkenyl, 5-9C cycloalkyl, 6-12C aryl (optionally substituted by one to three 1-4C alkyl or alkoxy, OH, halo, nitro, amino (optionally substituted by one or two 1-4C alkyl), or methylenedioxy) or indol-3-yl);

European Patent 46953 published Mar. 10, 1982 discloses N-amino acyl-indoline and tetrahydro isoquinoline carboxylic acids which are angiotensin coverting enzyme inhibitors and have the formula

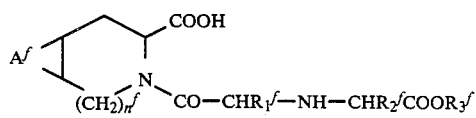

n$^f$ is 0 or 1;

A$^f$ ⌐⌐ is a benzene or cyclohexane ring:

R$_1^f$ and R$_2^f$ are each 1-6C alkyl, 2-6C alkenyl, 5-7C cycloalkyl, 5-7C cycloalkenyl, 7-12C cycloalkylalkyl, optionally partially hydrogenated 6-10C aryl, 7-14C aralkyl or 5-7 membered monocyclic or 8-10 membered bicyclic heterocyclyl containing 1 or 2 S or O and/or 1-4N atoms; all R$_1^f$ and R$_2^f$ groups are optionally substituted, R$_3^f$ is H, 1-6C alkyl, 2-6C alkenyl or 7-14C aralkyl.

The following Table II lists ACE inhibitors preferred for use in the combination of this invention.

TABLE II

PREFERRED ACE INHIBITORS $$\begin{array}{ccc} \text{COOR}^1 & \text{R}^2 & \text{O} \\ | & | & \| \\ \text{R—CH—NH—CH—C—R}^3 \end{array}$$

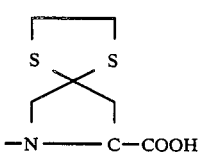

|  | R | R$_1$ | R$_2$ | R$_3$ |
|---|---|---|---|---|
| spirapril | C$_6$H$_5$CH$_2$CH$_2$— | Et | CH$_3$ | (S,S-dithiolane-prolyl structure) |
| enalapril | C$_6$H$_5$CH$_2$CH$_2$— | Et | CH$_3$ | prolyl |

TABLE II-continued

| | | | | |
|---|---|---|---|---|
| ramipril | C₆H₅CH₂CH₂— | Et | CH₃ | bicyclic [cyclopentane-fused pyrrolidine]—N—C—COOH |
| perindopril | CH₃CH₂CH₂ | Et | CH₃ | bicyclic [cyclohexane-fused]—N—C—COOH |
| indolapril | C₆H₅CH₂CH₂— | Et | CH₃ | bicyclic [cyclohexane-fused]—N—C—COOH |
| lysinopril | C₆H₅CH₂CH₂— | H | NH₂(CH₂)₄— | prolyl |
| CI-925 | C₆H₅CH₂CH₂— | Et | CH₃ | dimethoxybenzyl tetrahydroisoquinoline —N—C—COOH |
| pentopril (NH = CH₂) | CH₃ | Et | CH₃ | indane —N—C—COOH |
| cilazapril | C₆H₅CH₂CH₂— | H | $\underset{\underset{CH-C-R_3}{\overset{R_2\; O}{|\;\;\;||}}}{}$ | bicyclic diazabicyclic CO₂H |

$$RS-CH_2-\underset{\underset{CH_3}{|}}{CH}-CH_2-\overset{O}{\overset{||}{C}}-R^2$$

| | R | R₂ |
|---|---|---|
| catopril | H | prolyl |
| zofenopril | C₆H₅CO— | pyrrolidine with SC₆H₅ substituent —N—C—COOH |
| pivalopril | (CH₃)₃C—C(=O)— | cyclopentyl —N—CH₂—COOH |

$$R-\underset{\underset{OR^1}{|}}{\overset{\overset{O}{||}}{P}}-CH_2-\overset{\overset{O}{||}}{C}-N-\underset{\underset{}{}}{\overset{\overset{R^2}{|}}{C}}-COOH$$

TABLE II-continued

| | R | R¹ | R² |
|---|---|---|---|
| fosinopril | $C_6H_5-(CH_2)_4-$ | $-CH-O-\underset{\underset{O}{\|\|}}{C}-CH_2CH_3$ with side chain $-CH(CH_3)_2$ on CH | $C_6H_5-$ |

We have found that the novel compounds of the present invention are effective in treting congestive heart failure and various types of hypertension, particularly volume expanded hypertension. These novel compounds as well as other mercapto-acylamino acids known in the art have been found to enhance both the magnitude and duration of the antihypertensive and natriuretic effects of endogenous ANF. Administration of a combination of a mercapto-acylamino acid and an ACE inhibitor provides an antihypertensive effect greater than either the mercapto-acylamino acid or ACE inhibitor alone. Administration of a combination of a mercapto-acylamino acid of formula I and an exogenous ANF or ACE inhibitor is therefore particularly useful in treating hypertension.

In addition to the compound aspect, the present invention therefore also relates to treating hypertension with a mercapto-acylamino acid of formula I or with a mercapto-acylamino acid of formula I in combination with an ANF or an ACE inhibitor, which methods comprise administering to a mammal in need of such treatment an antihypertensive effective amount of the mercapto-acylamino acid or an antihypertensive effective amount of a combination of a mercapto-acylamino acid and an ANF or ACE inhibitor. The drug or combination of drugs is preferably administered in a pharmaceutically acceptable carrier, e.g. for oral or parenteral administration. The combinations of drugs may be co-administered in a single composition, or components of the combination therapy may be administered separately. Where the components are administered separately, any convenient combination of dosage forms may be used, e.g. oral mercapto-acylamino acid/oral ANF, oral mercapto-acylamino acid/parenteral ACE inhibitor, parenteral mercapto-acylamino acid/oral ANF, parenteral mercapto-acylamino acid/parenteral ACE inhibitor.

When the components of a combination of a mercapto-acylamino acid and an ANF are administered separately, it is preferred that the mercapto-acylamino acid be administered first.

The present invention also relates to a pharmaceutical composition comprising a mercapto-acylamino acid for use in treating hypertension, to a pharmaceutical composition comprising both a mercapto-acylamino acid and an ANF and to a pharmaceutical composition comprising both a mercapto-acylamino acid and an ACE inhibitor.

The antihypertensive effect of mercapto-acylamino acids was determined according to the following procedure:

Male Sprague Dawley rats weighing 100–150 g were anesthetized with ether and the right kidney was removed. Three pellets containing DOC acetate (desoxycorticosterone acetate, DOCA, 25 mg/pellet) were implanted subcutaneously. Animals recovered from surgery, were maintained on normal rat chow and were allowed free access to a fluid of 1% NaCl and 0.2% KCl instead of tap water for a period of 17–30 days. This procedure results in a sustained elevation in blood pressure and is a slight modification of published procedures (e.g. Brock et al., 1982) that have been used to produce DOCA salt hypertension in the rat.

On the day of study, animals were again anesthetized with ether and the caudal artery was cannulated for blood pressure measurement. Patency of the caudal artery cannula was maintained with a continuous infusion of dextrose in water at a rate of 0.2 ml/hr. Animals were placed into restraining cages where they recovered consciousness. Blood pressure was measured from caudal artery catheter using a Statham pressure transducer attached to a Beckman oscillographic recorder. In addition, a cardiovascular monitoring device (Buxco Electronics, Inc.) and a digital computer were used to calculate average blood pressures.

After an equilibration period of at least 1.5 hr., animals were dosed subcutaneously (1 ml/kg) with vehicle (methylcellulose, hereinafter MC) or mercapto-acylamino acid and blood pressure was monitored for the next 4 hours.

A similar procedure can be used to determine the effect of mercaptoacylamino acids in combination with ACE inhibitors.

The antihypertensive effect of mercapto-acylamino acids in combination with ANF can be determined according to the following procedures:

Male spontaneously hypertensive rats (SHR), 16–18 weeks old, 270–350 g, are anesthetized with ether and the abdominal aorta was cannulated through the tail artery. The animals are then placed into restrainers to recover from anesthesia (in less than 10 min.) and remain inside throughout the experiments. Through a pressure transducer (Gould P23 series) analog blood pressure signals are registered on a Beckman 612 recorder. A Buxco digital computer is used to obtain mean arterial pressures. Patency of the arterial cannula is maintained with a continuous infusion of 5% dextrose at 0.2 ml/hr. Animals were allowed a 90-min equilibration period. The animals first undergo a challenge with an ANF such as atriopeptin II (AP II) or AP28 30 µg/kg iv and at the end of 60 min. are treated with drug vehicle or a mercapto-acylamino acid subcutaneously. A second ANF challenge is administered 15 min. later and blood pressure is monitored for the next 90 min.

The antihypertensive effect is SHR of mercapto-acylamino acids and ACE inhibitors, alone and in combination, can be determined as follows:

Animals were prepared for blood pressure measurement as described above. After stabilization, animals were dosed subcutaneously or orally with test drugs or placebo and blood pressure is monitored for the next 4 hr.

The compounds having structural formula I have also been found to inhibit the activity of enzymes designated enkephalinases. The compounds are particularly useful for the inhibition of enkephalinase A, which is derived from the striata of both rats and humans. In in vitro tests, using test procedures for enkephalinase A inhibition well known to those skilled in the art, selected compounds having structural formula I have been found to inhibit the activity of the aforementioned enzyme. Therefore, the present invention also relates to a method of inhibiting the action of enkephalinases in a mammal thereby to elicit an analgesic effect with a compound of formula I, and to analgesic pharmaceutical compositions comprising compounds of formula I.

The compositions of this invention comprise a mercapto-acylamino acid or a mercapto-acylamino acid and an ANF or a mercapto-acylamino acid and an ACE inhibitor in combination with a pharmaceutically acceptable carrier for administration to mammals. A variety of pharmaceutical forms is suitable, preferably for oral or parenteral administration, although mechanical delivery systems such as transdermal dosage forms are also contemplated.

The daily hypertensive dose of the compound or combinations of this invention is as follows: for mercapto-acylamino acids alone the typical dosage is 1 to 100 mg/kg of mammalian weight per day administered in single or divided dosages; for the combination of mercapto-acylamino acid and an ANF, the typical dosage is 1 to 100 mg of mercapto-acylamino acid/kg mammalian weight per day in single or divided dosages plus 0.001 to 0.1 mg ANF/kg of mammalian weight per day, in single or divided dosages, and for the combination of mercapto-acylamino acid and an ACE inhibitor, the typical dosage is 1 to 100 mg of mercapto-acylamino acid/kg mammalian weight per day in single or divided dosages plus 0.1 to 30 mg ACE inhibitor/kg of mammalian weight per day in single or divided dosages. The exact dose of any component or combination to be administered is determined by the attending clinician and is dependent on the potency of the compound administered, the age, weight, condition and response of the patient.

Generally, in treating humans having hypertension, the compounds or combinations of this invention may be administered to patients in a dosage range as follows: for treatment with mercapto-acylamino acids alone, about 10 to about 500 mg per dose given 1 to 4 times a day, giving a total daily dose of about 10 to 2000 mg per day; for the combination of mercapto-acylamino acid and ANF, about 10 to about 500 mg mercapto-acylamino acid per dose given 1 to 4 times a day and about 0.001 to about 1 mg ANF given 1 to 6 times a day (total daily dosage range of 10 to 2000 mg day and 0.001 to 6 mg/day, respectively); and for the combination of a mercapto-acylamino acid and an ACE inhibitor, about 10 to about 500 mg mercapto-acylamino acid per dose given 1 to 4 times a day and about 5 to about 50 mg ACE inhibitor given 1 to 3 times a day (total daily dosage range of 10 to 2000 mg/day and 5 to 150 mg/day, respectively). Where the components of a combination are administered separately, the number of doses of each component given per day may not necessarily be the same, e.g. where one component may have a greater duration of activity, and will therefore need to be administered less frequently.

To produce an analgesic effect, compounds of this invention will be administered in a dosage range of from about 1 to about 100 m.p.k. The doses are to be administered at intervals of from 3 to 8 hours. However, the quantity and frequency of dosage will depend upon such factors as the severity of the pain, the general physical condition of the patient, the age and weight of the patient, and other factors recognized by the skilled clinician.

Typical oral formulations include tablets, capsules, syrups, elixirs and suspensions. Typical injectable formulations include solutions and suspensions.

The typical acceptable pharmaceutical carriers for use in the formulations described above are exemplified by: sugars such as lactose, sucrose, mannitol and sorbitol, starches such as cornstarch, tapioca starch and potato starch; ceullulose and derivatives such as sodium carboxymethyl cellulose, ethyl cellulose and methyl cellulose; calcium phosphates such as dicalcium phosphate and tricalcium phosphate; sodium sulfate; calcium sufate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; non-ionic, cationic and anionic surfactants; ethylene glycol polymers; betacyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

Since the present invention relates to treatment of hypertension with a combination of active ingredients wherein said active ingredients may be administered separately, the invention also relates to combining separate pharmaceutical compositions in kit form. That is, two kits are contemplated, each combining two separate units: a mercapto-acylamino acid pharmaceutical composition and an ANF pharmaceutical composition in one kit and a mercapto-acylamino acid pharmaceutical composition and an ACE inhibitor pharmaceutical composition in a second kit. The kit form is particularly advantageous when the separate components must be administered in different dosage forms (e.g. oral and parenteral) or are administered at different dosage intervals.

Following are examples of procedures for preparing compounds of formula I.

PREPARATION 1

2-Acetylthiomethyl-3-Phenylpropionyl Chloride

Dissolve 10 g (42 mmole) of 2-acetylthiomethyl-3-phenyl propionic acid and 10 g (84 mmole) of thionyl chloride in 50 ml of toluene. Stir for 10 hrs. under nitrogen and concentrate in vacuo. Dissolve the residue in 50 ml of toluene and again concentrate in vacuo. Repeat this step five times to obtain the product as a light brown oil.

PREPARATION 2

2-Benzoylthiomethyl-3-Phenylpropionyl Chloride

Using a procedure similar to that described in Example 1, substitute 2-benzoylthiomethyl-3-phenylpropionic acid for 2-acetylthiomethyl-3-phenyl propionic acid to give the title compound as a light yellow oil.

PREPARATION 3

3-tert-Butyloxycarbonylamino Benzoic Acid

To a solution of 12.3 g of 3-aminobenzoic acid in 75 ml of DMF, add 90 ml of 1N sodium hydroxide solution. Cool this solution in ice and add 22.8 g of di-tert-butyldicarbonate. Stir the solution for 41 hrs., concentrate in vacuo and dissolve the residue in a mixture of 200 ml each of ethylacetate and ice water. With stirring, adjust the pH to 3.0 with 20% aqueous citric acid. Separate the organic layer and wash it 4 times with 50 ml of 10% aqueous citric acid followed by 50 ml of saturated sodium chloride solution. Dry the organic layer over magnesium sulfate and concentrate in vacuo. Triturate the residue with hexane to give 3-tert-butyloxycarbonylaminobenzoic acid as a white solid.

PREPARATION 4

1-Methyl-4-(3'-Aminophenylcarbonyl)Piperazine Hydrochloride

Dissolve 3.0 g of the product of Preparation 3, 1.3 g of N-methylpiperazine, 1.9 g of 1-hydroxybenzotriazole and 2.7 g of 1-(3-dimethylaminopropyl)-3-ethylcarbodiimide hydrochloride in 10 ml of DMF. Stir for 18 hrs. and then concentrate in vacuo. Dissolve the resultant residue in 100 ml of ethyl acetate, wash with 20 ml of 1N NaHCO$_3$ solution, and 20 ml of saturated sodium chloride solution. Dry the organic layer over MgSO$_4$, filter and concentrate in vacuo. Dissolve 1.68 g of this residue in 10 ml of HCl:dioxane and stir for 2 hrs. Concentrate in vacuo to obtain the title compound as a white solid, mass spec M+ =219.

PREPARATION 5

3-Amino-N-[2-(4-Morpholino)ethyl]Benzamide Hydrochloride

Using the procedure of Preparation 4, replace N-methylpiperazine with 4-(2-aminoethyl)morpholine to obtain the title compound as a white solid, mass spec M+ =249.

PREPARATION 6

3-Amino-N-[2-(4-Pyridyl)ethyl]Benzamide Hydrochloride

Using the procedure of Preparation 4, replace N-methylpiperizine with 4-(2-aminoethyl)pyridine to obtain the title compound as a white solid, mass spec M+ =241.

EXAMPLE 1

N-[2-Benzoylthiomethyl-3-Phenylpropionyl]-3-Aminobenzoic Acid

Dissolve 0.2 g of the acid chloride from Preparation 2 and 0.08 g of 3-aminobenzoic acid in 10 ml of pyridine. Stir for 10 hrs. under nitrogen and concentrate in vacuo. Dissolve the residue in warm ethylacetate and cool to cause crystallization of the title compound as a white solid, m.p.=182°-184° C.

EXAMPLE 2

N-[2-Acetylthiomethyl-3-Phenylpropionyl]-3-Aminobenzoic Acid

Using a procedure similar to that of Example 1, substitute the acid chloride from Preparation 1 for the acid chloride from Preparation 2 to obtain the title compound, m.p. 169°-170° C. Elemental analysis: theoretical value for C$_{19}$H$_{19}$NO$_4$S is C=63.85, H=5.36, N=3.92, S=8.97; value found is C=63.75, H=5.22, N=3.69, S=9.02.

EXAMPLE 3

N-[2-Mercaptomethyl-3-Phenylpropionyl]-3-Aminobenzoic Acid

Slurry 0.5 g of the product of Example 1 in 5 ml of ethylacetate, purge with nitrogen for 30 min. and add 5 ml of a 1.0N solution of aqueous sodium hydroxide solution (also purged with nitrogen for 30 min.). Stir under nitrogen for 1 hr., then adjust to pH 2 with 1N HCl. Concentrate in vacuo until a precipitate forms. Filter, wash with water, and dry to obtain a white solid, m.p. 158°-163° C.

Alternatively, the title compound can be prepared using the same procedure as above, with the product of Example 2 is the starting material.

EXAMPLE 4

N-[2-Benzoylthiomethyl-3-Phenylpropionyl]-2-Aminobenzoic Acid

Using a procedure similar to that of Example 1, substitute 2-aminobenzoic acid for 3-aminobenzoic acid to obtain the title compound as a yellow oil. Thin layer chromatography (TLC) Rf=0.5 (silica gel; methylene chloride:methanol-acetic acid, 95:5:0.2).

EXAMPLE 5

N-[2-Mercaptomethyl-3-Phenylpropionyl]-2-Aminobenzoic Acid Ammonium Salt

Using the procedure of Example 3, substitute the product of Example 4 for the product of Example 1. Dissolve the crude product in 15 ml ether and bubble ammonia gas through the solution to obtain the title compound as a white solid, m.p.=60° C.(d).

EXAMPLE 6

N-[2-Acetylthiomethyl-3-Phenylpropionyl]-4-Aminobenzoic Acid

Using the procedure of Example 1, substitute 4-aminobenzoic acid for 3-aminobenzoic acid to obtain the title compound.

EXAMPLE 7

N-[2-Mercaptomethyl-3-Phenylpropionyl]-4-Aminobenzoic Acid

Using the procedure of Example 3, replace the product of Example 1 with the product of Example 6 to obtain the title compound as a white solid, m.p.=166°-168° C. TLC: Rf=0.6 (silica gel; dichloromethane:methanol:acetic acid, 95:4.5:0.5).

EXAMPLE 8

2-[[2-Acetylthiomethyl-3-Phenylpropionyl]-Amino]-Benzamide

Using the procedure of Example 1, replace 3-aminobenzoic acid with 2-aminobenzamide. Chromatograph the crude product on silica gel, eluting with ethyl acetate:hexane (1:1) to obtain the title compound as an amber oil, mass spec M+ =356.

EXAMPLE 9

3-[[2-Benzoylthiomethyl-3-Phenylpropionyl]-Amino]-Benzamide

Using the procedure of Example 1, replace 3-aminobenzoic acid with 3-aminobenzamide. Chromatograph the crude product on silica gel, eluting with ethyl acetate:hexane. Recrystallize the resulting solid from ethyl acetate:isopropyl ether to obtain the title compound as a white solid, m.p.=133°-135° C., mass spec M+ =418.

EXAMPLE 10

3-[[2-Acetylthiomethyl-3-Phenylpropionyl]-Amino]-Benzamide

Using the procedure of Example 2, replace 3-aminobenzoic acid with 3-aminobenzamide. Chromatograph the crude product on silica gel, eluting with ethyl acetate:ether (1:1). Recrystallize the resulting solid from ethyl acetate:isopropyl ether to obtain the title compound as a white solid, m.p. 141°-145° C., mass spec M+ =356.

EXAMPLE 11

3-[[2-Mercaptomethyl-3-Phenylpropionyl]-Amino]Benzamide

Using the procedure of Example 3, replace the product of Example 1 with the product of Example 10 to obtain the title compound as a white solid, m.p. 159°-164° C., mass spec M+ =314. Elemental analysis for $C_{17}H_{18}N_2O_2S$:

Theory: C, 64.96; H, 5.73; N, 8.90; Found: C, 64.16; H, 5.65; N, 8.30.

EXAMPLE 12

4-[[2-Acetylthiomethyl-3-Phenylpropionyl]-Amino]-Benzamide

Using the procedure of Example 1, replace 3-aminobenzoic acid with 4-aminobenzamide. Chromatograph the crude product on silica gel, eluting the ethyl acetate to obtain the title compound as a white solid, m.p.=195°-197° C., mass spec M+ =356.

EXAMPLE 13

4-[[2-Mercaptomethyl-3-Phenylpropionyl]Amino]Benzamide

Using the procedure of Example 3, replace the product of Example 1 with the product of Example 12 to give the title compound as a white solid, m.p.=195°-197° C., mass spec M+ =314.

EXAMPLE 14

6-[[2-Benzoylthiomethyl-3-Phenylpropionyl]-Amino]-3-Pyridinecarboxamide

Using the procedure of Example 1, replace 3-aminobenzoic acid with 6-amino-nicotinamide. Chromatograph the crude product on silica gel, eluting with ethyl acetate to obtain the title compound as a white solid, mass spec M+ =419.

EXAMPLE 15

6-[[2-Acetylthiomethyl-3-Phenylproionyl]-Amino]-3-Pyridinecarboxamide

Using the procedure of Example 2, replace 3-aminobenzoic acid with 6-aminonicotinamide. Chromatograph the crude product on silica gel, eluting with ethyl acetate to obtain the title compound as a white solid, mass spec M+ =357.

EXAMPLE 16

{2-Acetylthiomethyl-3-Phenyl-N-[3-(4-Methyl-1-Piperazinylcarbonyl)]Phenyl}Propionamide Hydrochloride Using the procedure of Example 2, replace 3-aminobenzoic acid with the product of Preparation 4. Chromatograph the crude product on silica gel, eluting with chloroform:methanol (10:1). Collect fractions having an Rf of 0.3 on silica gel TLC (chloroform:methanol, 10:1). Concentrate the desired fractions in vacuo, dissolve the residue in ethyl acetate and acidify with HCl gas. Filter the precipitate to obtain the title compound as a white solid, m.p.=98°-112° C., mass spec M+ =440.

EXAMPLE 17

{2-Mercaptomethyl-3-Phenyl-N-[3-(4-Methyl-1-Piperazinylcarbonyl)]Phenyl}Propionamide Hydrochloride Dissolve 1.25 of the product of Example 16 in 10 ml of methanol and purge with nitrogen for 30 min. Add 5.8 ml of 1N sodium hydroxide solution (also purged with nitrogen for 30 min.). Stir the resulting solution under nitrogen for one hr., add 5.8 ml of 1N HCl and concentrate in vacuo. Dissolve the resultant residue in 50 ml of ethyl acetate. Dry over MgSO$_4$, filter and concentrate in vacuo. Dissolve the residue in 50 ml of dioxane and acidify with HCl gas. Concentrate in vacuo to obtain the title compound as a white solid, m.p.=105°-120° C., mass spec M+ =397. Elemental analysis for $C_{22}H_{27}N_3O_2S$ HCl H$_2$O:

Theory: C, 58.53; H, 6.65; N, 9.30; Cl, 7.76; Found: C, 58.80; H, 6.22; N, 8.53; Cl, 7.44.

EXAMPLE 18

{2-Acetylthiomethyl-3-Phenyl-N-[3-[2-(4-Morpholinoethyl)Carbamoyl]Phenyl]}Propionamide Hydrochloride Using the procedure of Example 2, replace 3-aminobenzoic acid with the product of Preparation 5. Chromatograph the crude product on silica gel, eluting with dichloromethane:methanol (10:0.5). Collect fractions containing a product with an Rf of 0.5 on silica gel TLC (chloroform:methanol, 10:1). Combine the desired fractions and concentrate in vacuo. Dissolve the residue in ethyl acetate and acidify with HCl gas. Filter the resultant precipitate to obtain the title compound as a white solid, m.p.=100°-108° C., mass spec M+ =479.

EXAMPLE 19

{2-Mercaptomethyl-3-Phenyl-N-[3-[2-(4-Morpholinoethyl) Carbamoyl]Phenyl]}Propionamide Hydrochloride Using the procedure of Example 17, replace the product of Example 16 with the product of Example 18 to obtain the title compound.

EXAMPLE 20

{2-Acetylthiomethyl-3-Phenyl-N-[3-[2-(4-Pyridylethyl)Carbamoyl]Phenyl]}Propionamide Hydrochloride Using the procedure of Example 2, replace 3-aminobenzoic acid with the product of Preparation 6. Chromatograph the crude product on silica gel, eluting with dichloromethane:methanol(95:5). Dissolve the purified product in ethyl acetate and acidify with HCl gas to form a precipitate. Decant the solvent, triturate the resulting gum with ether and filter to give the title compound as a white solid, m.p.=94°–109° C., mass spec M+ =461.

EXAMPLE 21

{2-Mercaptomethyl-3-Phenyl-N-[3-[2-(4-Pyridylethyl)-Carbamoyl]Phenyl]}Propionamide Hydrochloride Using the procedure of Example 17, replace the product of Example 16 with the product of Example 20 to obtain the title compound.

Examples of formulations follow. "Active" refers to any mercapto-acylamino acid of formula I. "ACE inhibitor" refers to any of the ACE inhibitors listed earlier, especially those listed in the table of preferred ACE inhibitors. "ANF" refers to any atrial natriuretic factor especially those listed in Table 1.

EXAMPLE 22

| Tablets Formula No. | Ingredient | mg/tablet | mg/tablet |
|---|---|---|---|
| 1 | Active | 50 | 500 |
| 2 | Lactose | 122 | 213 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|  | Approximate Table Weight | 250 | 700 |

Method of Manufacture

Mix Items Nos. 1 and 2 in a suitable mixer for 10–15 minutes. Granulate the mixture with Item No. 3. Mill the damp granules through a coarse screen (e.g., ¼") if needed. Dry the damp granules. Screen the dried granules if needed and mix with Item No. 4 for 10–15 minutes. Add Item No. 5 and mix for 1–3 minutes. Compress the mixture to appropriate size and weight on a suitable tablet machine.

EXAMPLE 23

Sterile powder for injection:

|  | g/vial | g/vial |
|---|---|---|
| Active Sterile Powder | 0.5 | 1.0 |

Add sterile water for injection or bacteriostatic water for injection for reconstitution.

EXAMPLE 24

Injectable Solution:

| Ingredient | mg/ml | mg/ml |
|---|---|---|
| Active | 100 | 100 |
| Methylparaben | 1.8 | 1.8 |
| Propylparaben | 0.2 | 0.2 |
| Sodium Bisulfite | 3.2 | 3.2 |
| Disodium Edetate | 0.1 | 0.1 |
| Sodium Sulfate | 2.6 | 2.6 |
| Water for Injection q.s. ad | 1.0 ml | 1.0 ml |

Method of Manufacture

Dissolve parabens in a portion (85% of the final volume) of the water for injection at 65°–70° C. Cool to 25°–35° C. Charge and dissolve the sodium bisulfite, disodium edetate and sodium sulfate. Charge and dissolve the active. Bring the solution to final volume by adding water for injection. Filter the solution through 0.22µ membrane and fill into appropriate containers. Terminally sterilize the units by autoclaving.

EXAMPLE 25

| Tablets Formula No. | Ingredient | mg/tablet | mg/tablet |
|---|---|---|---|
| 1 | Active | 50 | 400 |
| 2 | ACE inhibitor | 25 | 50 |
| 3 | Lactose | 97 | 188 |
| 4 | Corn Starch, Food Grade, as a 10% Paste in Purified Water | 30 | 40 |
| 5 | Corn Starch, Food Grade | 45 | 40 |
| 6 | Magnesium Stearate | 3 | 7 |
|  | Approximate Table Weight | 250 | 700 |

Method of Manufacturing

Prepare the tablets as in Example 1.

EXAMPLE 26

ACE inhibitor Tablets

Substitute an ACE inhibitor for the active in Example 13.

EXAMPLE 27

| Tablets Formula No. | Ingredient | mg/tablet | mg/tablet |
|---|---|---|---|
| 1 | Active | 50 | 400 |
| 2 | ANF | 0.1 | 1 |
| 3 | Lactose | 121.9 | 212 |
| 4 | Corn Starch, Food Grade, as a 10% paste in Purified Water | 30 | 40 |
| 5 | Corn Starch, Food Grade | 45 | 40 |
| 6 | Magnesium Stearate | 3 | 7 |
|  |  | 250 | 700 |

Method of Manufacturing

Prepare the tablets as in Example 1.

EXAMPLE 28

| Tablets Formula No. | Ingredient | mg/tablet | mg/tabet |
|---|---|---|---|
| 1 | ANF | 0.1 | 1 |
| 2 | Lactose | 61 | 121 |
| 3 | Corn Starch, Food Grade, as a 10% paste in Purified Water | 15 | 30 |
| 4 | Corn Starch, Food Grade | 22.4 | 45 |
| 5 | Magnesium Stearate | 1.5 | 3 |
|  |  | 100 | 200 |

Method of Manufacture

Prepare tablets as in Example 1.

We claim:

1. A compound having the structural formula

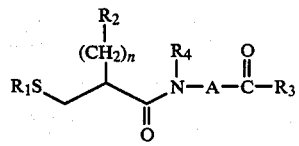

wherein
R₁ is H or R₅CO—;
R₂ is Y—C₆H₄—, Y—C₆H₄S—, Y—C₆H₄O—, Y—C₆H₄CH₂S—, Y—C₆H₄CH₂O—, α-naphthyl, β-naphthyl, β-naphthyl, diphenylmethyl or

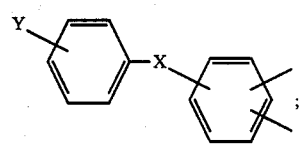

R₃ is —OR₆, —NR₆R₇ or

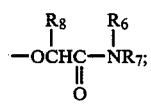

R₄ is hydrogen, lower alkyl or aryl lower alkyl;
R₅ is lower alkyl, hydroxylower alkyl, lower alkoxy lower alkyl; (di-lower alkyl) amino lower alkyl, Y₁—C₆H₄—lower alkyl, lower alkoxy, Y₁—C₆H₄—, naphthyl;
R₆ and R₇ are independently hydrogen, lower alkyl or substituted lower alkyl wherein the substituents are selected from the group consisting of 1 or 2 hydroxy groups, 1 or 2 lower alkoxy groups, lower alkoxy lower alkoxy, halogeno, halogeno lower alkoxy, amino, mono- or di-lower alkylamino, aryl, or substituted aryl wherein the substituents on aryl are 1-3 substituents selected from the group consisting of lower alkyl, hydroxy, halogeno, lower alkoxy and amino;
R₈ is hydrogen, alkyl, carboxyalkyl, mercaptoalkyl, alkylthioalkyl, aminoalkyl, hydroxyalkyl, phenylalkyl, hydroxyphenylalkyl, guanidinoalkyl, or carbamoylalkyl;
n is 0-3;
A is

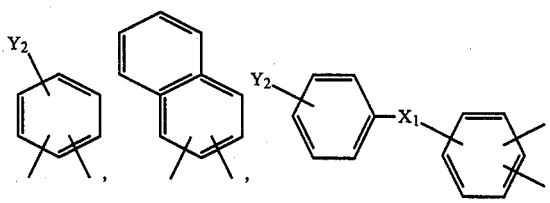

X and X₁ are independently a bond, —O—, —S—, or —CH₂—;
Y, Y₁ and Y₂ are independently 1 to 3 substituents selected from the group consisting of hydrogen, lower alkyl, cyclolower alkyl, lower alkoxy, OH, F, Cl, Br, I, —CN, —CO₂H, —CO₂—lower alkyl, —CH₂NH₂, —CONH₂ and aryl;
wherein aryl means mono-cyclic or fused ring bicyclic aromatic groups having 6 to 10 ring members or a pharmaceutically acceptable acid addition salt thereof.

2. A compound of claim 1 wherein R₄ is hydrogen.
3. A compound of claim 1 wherein n is 1.
4. A compound of claim 1 wherein R₄ is hydrogen and n is 1.
5. A compound of claim 4 wherein R₂ is Y—C₆H₄—.
6. A compound of claim 4 wherein R₁ is hydrogen, acetyl or benzoyl.
7. A compound of claim 4 wherein A is

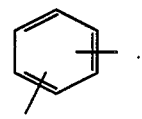

8. A compound of claim 4 wherein R₃ is OH, amino or —NR₆R₇ wherein one of R₆ and R₇ is hydrogen and the other is aryl lower alkyl.
9. A compound of claim 8 wherein R₂ is Y—C₆H₄, R₁ is hydrogen, benzoyl or acetyl and A is

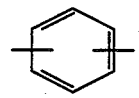

10. A compound of claim 8 wherein R₃ is OH or amino.
11. A compound of claim 1 named
N-[2-benzoylthiomethyl-3-phenylpropionyl]-3-aminobenzoic acid;
N-[2-acetylthiomethyl-3-phenylpropionyl]-3-aminobenzoic acid;
N-[2-mercaptomethyl-3-phenylpropionyl]-3-aminobenzoic acid;
N-[2-benzoylthiomethyl-3-phenylpropionyl]-2-aminobenzoic acid;
N-[2-mercaptomethyl-3-phenylpropionyl]-2-aminobenzoic acid;
N-[2-acetylthiomethyl-3-phenylpropionyl]-4-aminobenzoic acid;
N-[2-mercaptomethyl-3-phenylpropionyl]-4-aminobenzoic acid;
2-[[2-acetylthiomethyl-3-phenylpropionyl]-amino]-benzamide;
3-[[2-benzoylthiomethyl-3-phenylpropionyl]-amino]-benzamide;
3-[[2-acetylthiomethyl-3-phenylpropionyl]-amino]-benzamide;
3-[[2-mercaptomethyl-3-phenylpropionyl]-amino]-benzamide;
4-[[2-acetylthiomethyl-3-phenylpropionyl]-amino]-benzamide;
4-[[2-mercaptomethyl-3-phenylpropionyl]-amino]-benzamide.

12. A method for treating hypertension or congestive heart failure in mammals comprising administering to a mammal in need of such treatment an antihypertensive effective amount of a compound of claim 1.

13. An antihypertensive pharmaceutical composition comprising an antihypertensive effective amount of a compound of claim 1 in a pharmaceutically acceptable carrier.

14. The method for inhibiting the action of enkephalinases in a mammal thereby to elicit an analgesic effect comprising administering to a mammal in need of such treatment an analgesic-effective amount of a compound of claim 1.

15. A method for inhibiting the action of enkephalinases in a mammal thereby to elicit an analgesic effect comprising administering to a mammal in need of such treatment an analgesic-effective amount of a compound of claim 11.

16. An analgesic pharmaceutical composition comprising an analgesic-effective amount of a compound of claim 1 in a pharmaceutically acceptable carrier.

* * * * *

Disclaimer 4,879,309—*Ronald J. Doll*, Maplewood; *Bernard R. Neustadt*, West Orange, both of N. J. MERCAPTO-ACYLAMINO ACIDS AS ANTIHYPERTENSIVES. Patent dated Nov. 7, 1989. Disclaimer filed Apr. 8, 1991, by the assignee, Schering Corp.

Hereby enters this disclaimer to all claims of said patent.
[ *Official Gazette June 11, 1991* ]

REEXAMINATION CERTIFICATE (1748th)
United States Patent [19]
Doll et al.

[11] B1 4,879,309

[45] Certificate Issued Jul. 14, 1992

[54] MERCAPTO-ACYLAMINO ACIDS AS ANTIHYPERTENSIVES

[75] Inventors: Ronald J. Doll, Maplewood; Bernard R. Neustadt, West Orange, both of N.J.

[73] Assignee: Schering Corporation, Kenilworth, N.J.

Reexamination Request:
No. 90/002,263, Jan. 30, 1991

Reexamination Certificate for:
Patent No.: 4,879,309
Issued: Nov. 7, 1989
Appl. No.: 304,881
Filed: Jan. 30, 1989

Declaimer of Claims 1 to 16 Filed: Apr. 8, 1991
(1127 O.G. 36)

Related U.S. Application Data

[63] Continuation-in-part of Ser. No. 250,035, Sep. 27, 1988, abandoned.

[51] Int. Cl.$^5$ ............... A61K 31/24; A61K 31/195; C07C 321/16

[52] U.S. Cl. ................... 514/513; 514/522; 514/535; 514/562; 514/616; 558/254; 558/416; 560/16; 560/17; 560/18; 562/427; 562/432; 564/153; 564/154

[58] Field of Search ............... 562/432, 427; 558/254, 558/416; 560/16, 17, 18; 564/153, 154; 514/513, 522, 535, 562, 616

[56] References Cited
FOREIGN PATENT DOCUMENTS
890948 2/1982 Belgium.

*Primary Examiner*—Joseph P. Brust

[57] ABSTRACT

Novel mercapto-acylamino acids useful as analgesic, as well as in the treatment of hypertension and congestive heart failure and combinations of mercapto acylamino acids and atrial natriuretic factors or antiotensin converting enzyme inhibitors useful for treating hypertension and congestive heart failure are disclosed.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1 to 16 are now disclaimed.

* * * * *